US011560544B2

(12) United States Patent
Ben Hania et al.

(10) Patent No.: US 11,560,544 B2
(45) Date of Patent: Jan. 24, 2023

(54) **ISOLATION AND PURE CULTURE OF AN ARCHAEBACTERIUM OF ORDER *METHANOMASSILIICOCCALES***

(71) Applicants: LESAFFRE ET COMPAGNIE, Paris (FR); Université Clermont Auvergne, Clermont Ferrand (FR); Institut de recherche pour le développement, Marseilles (FR)

(72) Inventors: Wajdi Ben Hania, Ivry sur Seine (FR); Jean-François Brugere, Issoire (FR); Marie-Laure Fardeau, Pennes-Mirabeau (FR); Bernard Ollivier, Roquevaire (FR)

(73) Assignees: LESAFFRE ET COMPAGNIE, Paris (FR); UNIVERSITÉ CLERMONT AUVERGNE, Clermont Ferrand (FR); INSTITUT DE RECHERCHE POUR LE DÉVELOPPMENT, Marseilles (FR)

( * ) Notice: Subject to any disclaimer, the term of this patent is extended or adjusted under 35 U.S.C. 154(b) by 61 days.

(21) Appl. No.: 16/768,327

(22) PCT Filed: Nov. 30, 2018

(86) PCT No.: PCT/EP2018/083212
§ 371 (c)(1),
(2) Date: May 29, 2020

(87) PCT Pub. No.: WO2019/106181
PCT Pub. Date: Jun. 6, 2019

(65) Prior Publication Data
US 2021/0171898 A1 Jun. 10, 2021

(30) Foreign Application Priority Data
Dec. 1, 2017 (FR) ...................... 1761536

(51) Int. Cl.
*C12N 1/20* (2006.01)
*C12R 1/01* (2006.01)
(52) U.S. Cl.
CPC ............... *C12N 1/20* (2013.01); *C12N 1/205* (2021.05); *C12R 2001/01* (2021.05)
(58) Field of Classification Search
CPC ...... C12N 1/20; C12N 1/205; C12R 2001/01; A61K 35/741
See application file for complete search history.

(56) References Cited

U.S. PATENT DOCUMENTS

| | | | |
|---|---|---|---|
| 11,116,804 | B2 | 9/2021 | Strandwitz et al. |
| 2016/0040172 | A1* | 2/2016 | Burgard ............... C09D 147/00 524/17 |
| 2019/0070225 | A1 | 3/2019 | Strandwitz et al. |
| 2022/0040242 | A1 | 2/2022 | Strandwitz et al. |

FOREIGN PATENT DOCUMENTS

| | | |
|---|---|---|
| CN | 105385620 | 3/2016 |
| FR | 2990954 | 11/2013 |
| WO | WO-2013004933 | 1/2013 |

OTHER PUBLICATIONS

Widdel, F et al. Studies on dissimilatory sulfate-reducing bacteria that decompose fatty acids. I. Isolation of new sulfate-reducing bacteria enriched with acetate from saline environments. Description of *Desulfobacter postgatei* gen. nov., sp. nov. Arch. Microbiol. 1981. 129: 395-400. (Year: 1991).*
International Search Report dated Feb. 22, 2019 in International Application No. PCT/EP2018/083212.
Dridi, et al, "*Methanomassiliicoccus luminyensis* gen. nov., sp. nov., a methanogenic archaeon isolated from human faeces", Aug. 1, 2012, pp. 1902-1907, vol. 62, No. pt 8, International Journal of Systematic and Evolutionary Microbiology, XP055036209.
Lagier, et al, "Current and Past Strageegies for Bacterial Culture in Clinical Microbiology", Jan. 1, 2015, pp. 208-236, vol. 28, No. 1, Clinical Microbiology Reviews, XP008176967.
Fenn, Kathrin, "Mechanisms of Bacterial Uncultivability in the Human Gut Microbiome", Jan. 1, 2014, XP055479507.
Brugere, et al, "Archaebiotics", Oct. 31, 2013, pp. 5-10, vol. 5, No. 1, Gut Microbes, XP055342112.
Ben Hania, et al, "Archaebiotics: Archaea as Pharmabiotics for Treating Chronic Disease in Humans?", Oct. 11, 2017, Archaea—New Biocatalysts, Novel Pharmaceuticals and Various Biotechnological Applications XP055478651.
Fenn, et al, "Quinones are growth factors for the human gut microbiota", Dec. 20, 2017, pp. 1-11, vol. 5, No. 1, Microbiome, Biomed Central Ltd, XP021251933.
Borrel, et al, "Genome Sequence of "Candidatus Methanomethylophilus alvus" Mx1201, a Methanogenic Archeaon from the Human Gut Belonging to a Seventh Order of Methanogens", Dec. 2012, pp. 6944-6945, vol. 194, No. 24, Journal of Bacterriology.
Noel, et al, Draft Genome Sequence of "Candidatus Methanomethylophilus" sp. 1R26, Enriched from Bovine Rumen, a Methanogenic Archaeon Belonging to the Methanomassiliicoccales Order, Jan./Feb. 2016, pp. 1-2, vol. 4, issue 1, Genome Announcements.

* cited by examiner

*Primary Examiner* — David W Berke-Schlessel
*Assistant Examiner* — Susan E. Fernandez
(74) *Attorney, Agent, or Firm* — B. Aaron Schulman, Esq.; Stites & Harbison, PLLC

(57) ABSTRACT

The present invention concerns a process for isolating an archaeon of the order of commensal clade Methanomassiliicoccales, the use of a culture and/or isolation medium comprising a sterile extract of a bacterial culture of a bacterium of genus *Eggerthella*, for the isolation and/or culture of an archaeon of the order of commensal clade Methanomassiliicoccales, and a pure, isolated archaeon Methanomethylophilus alvus Mx-05. It also concerns a culture method of an archaeon of the order of commensal clade Methanomassiliicoccales.

18 Claims, No Drawings

ISOLATION AND PURE CULTURE OF AN ARCHAEBACTERIUM OF ORDER *METHANOMASSILIICOCCALES*

The present invention concerns a process for isolating an archaeon of the order of commensal clade Methanomassiliicoccales, the use of a culture and/or isolation medium comprising a sterile extract of a bacterial culture of a bacterium of genus *Eggerthella*, for the isolation and/or culture of an archaeon of the order of commensal clade Methanomassiliicoccales, and a pure, isolated archaeon Methanomethylophilus alvus Mx-05. It also concerns a culture method of an archaeon of the order of commensal clade Methanomassiliicoccales.

The taxonomic order of Methanomassiliicoccales, which are prokaryote microorganisms of archaeon type, is composed of 2 major clades (Söllinger et al, 2015; Borrel et al, 2017). One of these is almost exclusively formed of microorganisms living in the digestive tract of animals (from insects to man) called «host-associated cluster» or commensal clade. This clade particularly comprises natural members of the intestinal microbiota in man, and among these some are capable of converting trimethylamine (TMA) to methane using hydrogen as electron donor. TMA is a pro-atherogenic compound derived from the intestinal microbial metabolism of varied nutrients. The possible use of these organisms as probiotics, in particular for the prevention of cardiovascular disease («archaebiotics») by lowering intestinal TMA levels, has been described (Brugere et al, 2014). This in turn leads to a decrease in the plasma derivative of TMA (plasma TMA oxide or pTMAO) resulting from passage through the liver after intestinal absorption (hepatic oxidation by flavin-containing monooxygenases), a metabolite involved in various mechanisms contributing towards atherosclerosis. At the present time, there is no other component of the human intestinal microbiota that is known to be able to remediate TMA into a metabolite considered to be inert for man i.e. methane.

However, no representative of this group of microorganisms (commensal clade) having this bioremediation action has yet been isolated and obtained in pure culture.

Aside from technical issues related to anaerobic microbiology of these micro-organisms known to be highly sensitive to oxygen (EOS, Extremely Oxygen Sensitive), the usual practice to isolate this type of microorganism requires particular operating conditions. After enrichment is obtained whereby the methanogenic archaea become dominant, 2 approaches are applied: (i) «cloning» the culture using solid media via the Roll-tubes technique (Hungate, 1969) or (ii) dilutions/extinctions of the enrichment in a liquid medium for the removal in particular of non-methanogenic fermenting microorganisms.

Up until now, these techniques have proved to be inefficient for isolation, via axenic culture, of commensal clade Methanomassiliicoccales, irrespective of the isolation conditions used (reported in various scientific articles, in particular by Sollinger et al, 2015).

Yet, the availability of a pure strain and controlled growth thereof are prerequisites for the envisaging of therapeutic application.

In the present invention, the pure Mx-05 strain of the Methanomethylophilus alvus species has been isolated through a fully innovative approach.

The present invention concerns a pure, isolated archaeon (Archaea domain) Methanomethylophilus alvus Mx-05, a strain deposited on 18 Sep. 2017 under the Budapest Treaty with the Leibniz-Institut (DSMZ, Braunschweig, Germany) under number DSM32684 (Depositor: Université Clermont Auvergne, France).

It also concerns the use of a culture and/or isolation medium comprising a sterile extract of a bacterial culture of a bacterium of genus *Eggerthella* for the isolation and/or pure culture (axenic) of an archaeon of the order of commensal clade Methanomassiliicoccales. Advantageously, said culture and/or isolation medium comprises growth factor(s) obtained from said culture of a bacterium of genus *Eggerthella*.

The present invention further concerns a method for isolating an archaeon of the order of commensal clade Methanomassiliicoccales comprising:

a) inoculating a biological sample likely to contain an archaeon of the order of commensal clade Methanomassiliicoccales, preferably a sample of animal or human stools, under anaerobic conditions in a gaseous atmosphere containing dihydrogen $H_2$ under mesothermal conditions in a culture medium comprising (i) a base medium comprising $KH_2PO_4$, NaCl, $MgSO_4.7H_2O$, $NH_4Cl$, $CaCl_2.2H_2O$, sodium acetate, Cysteine-HCl, resazurin, a Widdel trace element solution, a selenite-tungstate solution, (ii) 2 $Na_2S$ and 10% $NaHCO_3$, a vitamin mixture (e.g. a Balch vitamin solution) to which are added (iii) one or more compounds providing amino acids such as Biotrypcase, peptone and/or casamino acids, yeast extract, and (iv) methylated compounds such as methylamines or methanol;

b) replacing the culture medium of step a) by an identical culture medium but depleted of compounds providing amino acids and to which vitamins are added;

c) detecting positive enriching with an archaeon of the order of commensal clade Methanomassiliicoccales in said inoculated sample, in particular via microscopy, methane production and $H_2$ consumption, PCR, qPCR or sequencing; and d) performing liquid serial dilutions or using the roll-tube technique of said positive enrichment obtained at step c) using a medium such as defined at step a) or b) to which is added a sterile extract of a bacterial culture of a bacterium of genus *Eggerthella* of the invention until a clone is obtained of an archaeon of the order of commensal clade Methanomassiliicoccales.

Finally, the invention concerns a culture method of an archaeon of the order of commensal clade Methanomassiliicoccales, pure or contained in a microbial consortium, comprising:

a) inoculating either a biological sample comprising an archaeon of the order of commensal clade Methanomassiliicoccales, preferably a sample or animal or human stools in a culture medium, or a pure archaeon of Methanomassiliicoccales order comprising (i) a base medium comprising $KH_2PO_4$, NaCl, $MgSO_4.7H_2O$, $NH_4Cl$, $CaCl_2.2H_2O$, sodium acetate, Cysteine-HCl, resazurin, a Widdel trace element solution, a selenite-tungstate solution, 2% $Na_2S$ and/or 10% $NaHCO_3$ to which is added (ii) one or more compounds providing amino acids such as Biotrypcase, peptone and/or casamino-acids, yeast extract, (iii) methylated compounds such as methylamines or methanol and (iv) a sterile extract of a bacterial culture of the bacterium of genus *Eggerthella*, according to the invention;

b) placing the inoculum obtained at step a) under anaerobic conditions in a gaseous atmosphere comprising dihydrogen $H_2$; and c) incubating under mesothermal conditions to reach an exponential growth phase with production of methane in at least 2 days, preferably no more than 15 days.

Archaeon Methanomethylophilus Alvus Mx-05

As mentioned above, the present invention concerns a pure, isolated archaeon Methanomethylophilus alvus Mx-05, a strain deposited on 18 Sep. 2017 under the Budapest Treaty with the Leibniz-Institut (DSMZ, Braunschweig, Germany) under number DSM32684 (Depositor: Université Clermont Auvergne, France).

This deposit was made by Université Clermont Auvergne, 49 boulevard Francois Mitterrand—63000 Clermont-Ferrand—France.

By «pure» is to be understood the meaning commonly employed by persons skilled in the art of the field of the invention. In particular, by pure it is meant the absence of contaminants and the sole presence of a strain, colony or clone or the archaeon Methanomethylophilus alvus Mx-05. Purity criteria are those usually used by skilled persons. In particular, in the present invention, the criteria are uniform cell morphology, production of methane, and no growth in a complex medium (SMS) containing carbon hydrates not consumed by the methanogenic archaeon, but allowing the evidencing of methanogenic contaminants if any.

By «isolated» is to be understood the meaning usually used by skilled persons in the field of the invention. An isolated archaeon Methanomethylophilus alvus Mx-05 will be an archaeon separated from the other archaea and/or bacteria and/or yeasts or other eukaryote contaminants potentially contained in the starting sample.

As mentioned in the foregoing, Methanomassiliicoccales are prokaryote microorganisms of Archea type composed of 2 major clades including the so-called «commensal» clade to which the above-mentioned strain belongs, formed almost exclusively of microorganisms living in the digestive tract of animals (from insects to man), said strain belonging to those able to convert TMA to methane using hydrogen as electron donor.

The pure, isolated archaeon Methanomethylophilus alvus Mx-05, a strain deposited on 18 Sep. 2917 under the Budapest Treaty with the Leibniz-Institut (DSMZ, Braunschweig, Germany) under number DSM32684 (Depositor: Université Clermont Auvergne, France) such as abovementioned can be obtained in particular with the method for isolating an archaeon of the order of commensal clade Methanomassiliicoccales according to the invention and/or can be the subject of the culture method of an archaeon of the order of commensal clade Methanomassiliicoccales according to the invention and/or can be isolated using a culture and/or isolation medium comprising a sterile extract of a bacterial culture of a bacterium of genus *Eggerthella*, such as demonstrated in the «Examples» section of the present invention.

Use of a Culture and/or Isolation Medium Comprising a Sterile Extract of a Bacterial Culture of a Bacterium of Genus *Eggerthella*, As aforementioned, the present invention also concerns the use of a culture and/or isolation medium comprising a sterile extract of a bacterial culture of a bacterium of genus *Eggerthella*, for the isolation and/or pure culture of an archaeon of the order of commensal clade Methanomassiliicoccales.

As above-mentioned and advantageously, said culture and/or isolation medium comprises growth factor(s) obtained from said culture of a bacterium of genus *Eggerthella*.

Said culture and/or isolation medium may further comprise any compound which might be useful for the culture or isolation of an archaeon of the order of commensal clade Methanomassiliicoccales.

In particular, the medium further comprises one or more compounds providing amino acids such as Biotrypcase, peptone and/or casamino acids, and yeast extract.

For example, the medium further comprises 0.5 to 50 g/L of Biotrypcase, peptone, casamino acids, yeast extract (in particular 10 g/L of each of these compounds). In addition, the medium may comprise coenzyme M. This o-factor is essential for methanogenesis. For the archaeon Methanomethylophilus alvus Mx-05, coenzyme M can be omitted.

Further particularly, the medium additionally comprises $KH_2PO_4$, NaCl, $MgSO_4.7H_2O$, $NH_4Cl$, $CaCl_2.2H_2O$, sodium acetate, Cysteine-HCl, resazurin, a Widdel trace element solution, selenite-tungstate solution, 2% $Na_2S$ and/or 10% $NaHCO_3$.

Further particularly also, the medium comprises methylated compounds such as methylamines or methanol.

By «methylamines», it is particularly meant mono-, di- or tri-methylamine.

One example of said medium called base medium is given in Table 3 in the Examples.

All these compounds are commercially available compounds and/or are well known to skilled persons.

For example, the base medium is prepared in a $N_2/CO_2$ gaseous atmosphere (80:20% v/v).

A tungstate-selenite solution has the following composition for example per litre: 0.4 g NaOH, 2 mg $Na_2SeO_3$ and 4 mg $Na_2WO_4.5H_2O$.

A Widdel trace element solution has the following composition for example and can be prepared as follows:

Ferrous chloride is dissolved in hydrochloric acid. Bi-distilled water is added, followed by the salts of the different trace elements. The pH is adjusted to between 7.1 and 7.3 with HCl or $Na_2CO_3$.

This solution of trace elements can be used for example in a proportion of 1 mL per litre of culture medium.

TABLE 1

| Composition of a Widdel trace element solution | |
|---|---|
| Nitrilotriacetic acid | 1.50 g |
| $MgCl_2, 6H_2O$ | 2.50 g |
| NaCl | 1.00 g |
| $MnCl_2, 4H_2O$ | 0.60 g |
| $FeCl_2, 4H_2O$ | 100.00 mg |
| $CoCl_2, 6H_2O$ | 100.00 mg |
| $CaCl_2, 2H_2O$ | 100.00 mg |
| $ZnCl_2$ | 100.00 mg |
| $CuCl_2, 2H_2O$ | 10.00 mg |
| $AlCl_3$ | 10.00 mg |
| $H_3BO_3$ | 10.00 mg |
| $Na_2MoO_4, 2H_2O$ | 10.00 mg |
| pH (adjusted with 10 M KOH solution) | 6.50 |
| $H_2O$ double distilled q.s. | 1000 mL |

The culture medium of the invention can be in the liquid state in which case it comprises distilled water, or in a freeze-dried state able to be regenerated through the addition of distilled water, or in the solid state in particular in gelled form and more particularly through the addition of agar, more particularly 2% final agar.

By «*Eggerthella*», it is meant an Actinobacteria bacterial genus of the Coriobacteriaceae family. The members of this genus are anaerobic bacilli, non-sporulate and non-mobile, Gram-positive which develop in isolated manner in pairs or in short chains. They are particularly found in the human colon.

In the present invention, the sterile extract of a bacterial culture of a bacterium of genus *Eggerthella* is particularly derived from a bacterium selected from among *Eggerthella lenta* or the strain called *Eggerthella* sp. Eg01-Mx05 deposited on 13 Jul. 2017 under the Budapest Treaty with the Leibniz-Institut (DSMZ, Braunschweig, Germany) under number DSM 32565.

This deposit was made by Universite Clermont Auvergne, 49 boulevard Francois Mitterrand—63000 Clermont-Ferrand—France.

By «sterile extract» is to be understood the meaning usually used by skilled persons in the technical field of the invention i.e. free of any viable organism.

In particular, in the present invention the sterile extract is obtained with any technique known to skilled persons provided that it does not deteriorate the biological activity of the extract. Sterilisation via filtration for example on a 0.22 μm filter, autoclaving e.g. direct autoclaving on the bacterial culture of a bacterium of genus *Eggerthella* with direct use of the solution thus obtained, or direct autoclaving of the bacterial culture of a bacterium of genus *Eggerthella* followed by centrifugation of the solution thus obtained, or the use of an antibiotic on completion of the culture of a bacterium of genus *Eggerthella* whether or not coupled with a centrifugation and/or filtration step, can be cited as examples.

In particular, in the present invention, the sterile extract is a bacterial filtrate of a bacterium of genus *Eggerthella*.

By «filtrate» it is meant the meaning usually employed by skilled persons i.e. here the liquid collected after the filtration step through a filter of porosity preventing the passing of living cells.

In particular, in the present invention, the filtrate of a culture of the bacterium of genus *Eggerthella* is prepared following the method comprising:

a) cultivating a bacterium of genus *Eggerthella* in a medium such as the conventional media ATCC 260 or 1490 and DSMZ 78 or 209, said medium comprising Biotrypcase, yeast extract, peptone, amino acids, meat extract, hemin and/or vitamin K1 or K3; and simple sugars;

b) incubating the culture medium comprising said bacterium at a temperature of 20 to 40° C., preferably at 37° C., for at least 1 day, preferably no more than 15 days;

c) filtering the culture medium comprising said bacterium, preferably using filters preventing the passing of living organisms, in particular on a filter having a pore size of 0.2 μm; and d) collecting the filtrate obtained after step c).

By «simple sugars», it is meant monosaccharides having 5 or 6 carbon atoms e.g. glucose.

In particular, the culture medium at step a) of the method for preparing the filtrate comprises 0.5 to 50 g/L for example of Biotrypcase, peptone, casamino acids, yeast extract (preferably 10 g/L) and 0 to 100 mM glucose (preferably 20 mM).

The temperature mentioned at step b) is between 20 and 40° C. For example, it is therefore between 30 and 40° C. or between 35 and 40° C. It is therefore 21, 22, 25, 27, 28, 30, 32, 34, 35, 36, 37, 38, 39° C. for example, in particular 37° C.

Incubation is conducted using any technique known to skilled persons, under anaerobic conditions, such as those described for example for the species *Eggerthella lenta* by microorganism collection organizations such as ATCC or DSMZ.

Incubation lasts at least 1 day and preferably no more than 15 days. For example, incubation time is 1, 2, 3, 4, 5, 6, 7, 8, 9, 10, 11, 12, 13, 14 or 15 days, in particular 7 days.

Sterilisation by filtration mentioned at step c) of the method for preparing a bacterial filtrate can be replaced by any technique known to skilled persons allowing the extract of the invention to be obtained in sterile form, provided that the method used does not deteriorate the biological activity of the extract.

Regarding the bacterial filtrate, it is prepared for example by filtration through a filter preferably using filters preventing the passing of living organisms, in particular a filter having a pore size of 0.2 μm, and more particularly a filter having a pore size of 0.22 μm. These filters are commercially available e.g. Basix™ radiosterilized filters by Fisher Scientific in PES (polyethersulfone), of diameter 25 mm (Ref: 13-100-106, Fisher Scientific) adaptable to syringes (Ref: SLGP033RS by Merck).

Step c) particularly allows the removal of any living *Eggerthella* cell or any other possible viable contaminant.

The filtrate is collected after step c) under conditions allowing good storage thereof, in particular in an anaerobic atmosphere at ambient temperature or at 4° C. if storage periods extend over several months.

In particular, for the use according to the present invention the archaeon of the order of commensal clade Methanomassiliicoccales is a Methanomethylophilus alvus archaeon, in particular a pure, isolated Methanomethylophilus alvus Mx-05 archaeon, more particularly the strain deposited on 18 Sep. 2017 under the Budapest Treaty with the Leibniz-Institut (DSMZ, Braunschweig, Germany) under number DSM32684 (Depositor: Université Clermont Auvergne, France).

Method for Isolating an Archaeon of the Order of Commensal Clade Methanomassiliicoccales.

As mentioned above, the present invention also concerns a method for isolating an archaeon of the order of commensal clade Methanomassiliicoccales comprising:

a) inoculating a biological sample likely to comprise an archaeon of the order of commensal clade Methanomassiliicoccales, preferably a sample of animal or human stools, under anaerobic conditions in a gaseous atmosphere containing dihydrogen $H_2$ under mesothermal conditions in a culture medium comprising (i) a base medium comprising $KH_2PO_4$, NaCl, $MgSO_4.7H_2O$, $NH_4Cl$, $CaCl_2.2H_2O$, sodium acetate, Cysteine-HCl, resazurin, a Widdel trace element solution, a selenite-tungstate solution, (ii) 2 $Na_2S$ and 10% $NaHCO_3$, a vitamin mixture (e.g. Balch vitamin solution), to which are added (iii) one or more compounds providing amino acids such as Biotrypcase, peptone and/or casamino-acids, yeast extract, and (iv) methylated compounds such as methylamines or methanol;

b) replacing the culture medium of step a) by an identical culture medium but depleted of compounds providing amino acids and to which vitamins are added;

c) detecting positive enrichment with an archaeon of the order of commensal clade Methanomassiliicoccales in said inoculated sample, in particular via microscopy, methane production and $H_2$ consumption, PCR, qPCR or sequencing; and d) performing liquid serial dilutions or the roll-tube technique of said positive enrichment obtained at step c) using a medium such as defined at step a) or b) to which is added a sterile extract of a bacterial culture of a bacterium of genus *Eggerthella* according to the invention until a clone is obtained of an archaeon of the order of commensal clade Methanomassiliicoccales.

In particular, the method of the invention further comprises a step c') between step c) and step d), at which the culture medium comprising the biological sample is filtered, preferably on a filter having a pore size of at least 0.45 µm, advantageously of 0.45 µm, the filtrate obtained after this step c') being subsequently used at step d) to carry out the serial dilutions.

The filtration step, preferably on a filter having a pore size of at least 0.45 µm, is optional: it allows an increase in the proportion of commensal clade Methanomassiliicoccales relative to the other microbes present, since this clade is composed of small-size cells (approximately 0.5 µm+/−0.2) which partly pass through the filter, contrary to numerous non-desired cells. This step promotes/accelerates enriching with Methanomassiliicoccales.

By «inoculation» it is to be understood the usual meaning used by skilled persons in the technical field of the invention, in particular the action of seeding the culture medium with the biological sample, here under anaerobic conditions.

By «biological sample» is meant a human or animal sample, in particular of human or animal stools.

By «anaerobic conditions» it is to be understood the meaning known to persons skilled persons in the technical field of the invention, in particular conditions under which there is no oxygen in dioxygen form.

By «gaseous atmosphere» it is meant for example an atmosphere formed of dihydrogen (in particular 2 bar).

By «mesothermal conditions» it is meant a temperature of between 20 and 40° C., for example between 30 and 40° C. or between 35 and 40° C. The temperature is therefore 21, 22, 25, 27, 28, 30, 32, 34, 35, 36, 37, 38, 39° C. for example, in particular 37° C.

The term «base medium» is a term commonly used by skilled persons in the technical field of the invention, and designates a medium comprising the compounds required for culture of the archaeon under the conditions set forth above. Said medium is described in detail for example in Table 3 of the Examples. A Widdel trace element solution and a selenite-tungstate solution are defined in the preceding section relating to the use of a culture and/or isolation medium comprising a bacterial filtrate of a bacterium of genus *Eggerthella*, The compounds included in the composition of the base medium are commercially available compounds and well known to skilled persons.

For example, the base medium is prepared in a gaseous $N_2/CO_2$ atmosphere (80:20% v/v).

The base culture medium can be in the liquid state in which case it comprises distilled water, or in a freeze-dried state able to be fully or partly regenerated through the addition of distilled water, or in the solid state in particular in gelled form more particularly through the addition of agar, more particularly 2% final agar.

As mentioned above, the biological sample is inoculated into a base medium to which compounds are added providing amino acids such as Biotrypcase, peptone and/or casamino acids, yeast extract and methylated compounds.

Therefore, in one embodiment of the isolation process of the invention, the biological sample is inoculated into a base medium to which are added Biotrypcase, peptone, casamino acids, yeast extract and methylated compounds.

The methylated compounds are methanol and/or methylamines for example. By «methylamines», is meant for example mono-, di- and/or tri-methylamine.

In one embodiment of the process of the invention, 1 g/L of yeast extract and 10 to 80 mM of simple methylated compounds are added to the base medium.

In one embodiment of step a) of the above-mentioned isolation process, the biological sample comprises an archaeon of the order of commensal clade Methanomassiliicoccales.

As indicated at step b) of the isolation process of the invention, the culture medium of step a) is replaced by an identical culture medium but depleted of compounds providing amino acids such as Biotrypcase, peptone and/or casamino acids, yeast extract, and to which vitamins are added.

By «depleted» it is meant that the concentration of compounds providing amino acids such as Biotrypcase, peptone or casamino acids and yeast extract in the medium is lower than the concentration initially contained at step a). This concentration can even be zero i.e. the compounds providing amino acids such as Biotrypcase, peptone and/or casamino acids, and yeast extract can be absent in this second medium.

The vitamins which can be added are vitamins known to be suitable by skilled persons.

For example, a Balch vitamin solution can be cited (Balch et al, 1979).

Said solution can be prepared as indicated below with the composition mentioned in Table 2, in mg per litre of distilled water:

TABLE 2

| | |
|---|---|
| Biotin | 2 |
| Folic acid | 2 |
| Pyridoxine hydrochloride | 10 |
| Thiamine hydrochloride | 5 |
| Riboflavin | 5 |
| Nicotinic acid | 5 |
| Calcium pantothenate | 5 |
| Vitamin B12 | 0.1 |
| p-aminobenzoic acid | 5 |
| Lipoic acid | 5 |

The culture medium of step a) can be replaced after 3 to 15 days, for example after 3, 4, 5, 6, 7, 8, 9, 10, 11, 12, 13, 14, 15 days, or the culture medium of step a) is replaced by the medium of step b) as a function of the monitoring results of a growth indicator of Methanomassiliicoccales, for example as soon as the regular recording of methane production of the strain indicates the onset of a plateau.

As indicated in the above-mentioned isolation process, the abundance of the archaeon of the order of commensal clade Methanomassiliicoccales is verified by one of the techniques mentioned at step c).

These techniques are all techniques well known to skilled persons for the detection of enrichment.

Microscopy allows determination of cell forms, measurement of methane and $H_2$ is performed for example by gas phase chromatography, qPCR allows quantification of populations, and sequencing allows determination of the dominant enrichment species. These techniques can be used individually or together. Sequencing is the sequencing in particular of general or specific molecular markers (e.g. 16S and mcrA, genes respectively encoding 16S RNA of the small 16S ribosomal subunit and the alpha subunit of the methyl-coenzyme M reductase specific to methanogenesis), or a shotgun metagenomic sequencing approach.

Isolation as such is then performed at step d) of the above-mentioned method.

The medium enriched with an archaeon of the order of commensal clade Methanomassiliicoccales is diluted via liquid or solid dilutions i.e. using dilution techniques in liquid medium known to skilled persons e.g. in Hungate tubes containing culture medium, or solid medium dilution techniques (roll-tubes also containing culture medium). Dilutions are carried out until a clone is obtained of an archaeon of the order of commensal clade Methanomassiliicoccales.

«Clone» is used in the same manner as «strain D, the isolation process of the invention at its final step being intended to isolate a pure strain of archaeon of the order of commensal clade Methanomassiliicoccales.

The culture medium used at step d) is a medium such as defined at step a) or b) to which there is added a sterile extract of a bacterial culture of a bacterium of genus *Eggerthella* such as defined in the present invention.

The culture medium can therefore comprise a base medium free of complex organic compounds (compounds providing amino acids) but comprising vitamins, or a base medium comprising one or more compounds providing amino acids such as Biotrypcase, peptone and/or casamino acids, yeast extract e.g. in a concentration of 2 g/L, and methylated compounds.

Regarding solid dilutions, it is possible to subculture the colonies obtained in a liquid medium and then to re-dilute these in a liquid medium, the last positive liquid dilution representing the isolated strain.

In particular, in the isolation process of the invention, determination of the obtaining of a clone of an archaeon of the order of commensal clade Methanomassiliicoccales is performed via microscopy, methane production and $H_2$ consumption, qPCR or sequencing. In particular, sequencing is sequencing of general or specific molecular markers (e.g. 16S and mcrA, genes respectively encoding 16S RNA of the small 16S ribosomal subunit and the alpha subunit of the methyl-coenzyme M reductase specific to methanogenesis), or a shotgun metagenomic sequencing approach.

In addition, as above-mentioned, in one embodiment of the method of the invention, the method of the invention further comprises a step c') between step c) and step d), at which the culture medium comprising the biological sample is filtered. The filtration step is performed using any technique known to skilled persons in the technical field of the invention.

In particular, filtration is performed on a filter having a pore size of at least 0.45 µm, advantageously of 0.45 µm. These filters are commercially available e.g. from Fisher Scientific, in the form of Basix™ sterile 0.45 µm filters in PES (polyethersulfone) (Reference 13-100-107).

The filtrate obtained after this step c') is subsequently used at step d) to obtain the serial dilutions.

In particular, in the method of the present invention, the sterile extract of a bacterial culture of a bacterium of genus *Eggerthella* is a bacterial filtrate of a bacterium of genus *Eggerthella*.

More particularly, said filtrate is prepared following the method comprising:

a) culturivating a bacterium of genus *Eggerthella* in a medium e.g. conventional media such as ATCC 260 or 1490 and DSMZ 78 or 209, said medium comprising Biotrypcase, yeast extract, peptone, amino acids, meat extract, hemin, and/or vitamin K1 or K3, and simple sugars.

b) incubating the culture medium comprising said bacterium at a temperature of 20 to 40° C., preferably at 37° C., for at least 1 day, preferably no more than 15 days;

c) filtering the culture medium comprising said bacterium, preferably using filters preventing the passing of living organisms, in particular on a filter having a pore size of 0.2 µm; and d) collecting the filtrate obtained after step c).

This method is defined in the preceding section on the use of a culture and/or isolation medium comprising a sterile extract of bacterial culture of a bacterium of genus *Eggerthella*, In particular, in the present invention, the archaeon of the order of commensal clade Methanomassiliicoccales is an archaeon of Archaea Methanomethylophilus alvus, in particular a pure, isolated Archaea Methanomethylophilus alvus Mx-05, a strain deposited on 18 Sep. 2017 under the Budapest Treaty with the Leibniz-Institut (DSMZ, Braunschweig, Germany) under number DSM32684 (Depositor: Université Clermont Auvergne, France).

Culture Method of an Archaeon of the Order of Commensal Clade Methanomassiliicoccales.

As aforementioned, the present invention also concerns a culture method of an archaeon of the order of commensal clade Methanomassiliicoccales that is pure or contained in a microbial consortium, comprising:

a) inoculating either a biological sample comprising an archaeon of the order of commensal clade Methanomassiliicoccales, preferably a sample of animal or human stools, or a pure archaeon of the order Methanomassiliicoccales, into a culture medium comprising a base medium comprising $KH_2PO_4$, NaCl, $MgSO_4.7H_2O$, $NH_4Cl$, $CaCl_2.2H_2O$, sodium acetate, Cysteine-HCl, resazurin, a Widdel trace element solution, a selenite-tungstate solution, 2% $Na_2S$ and/or 10% $NaHCO_3$, to which are added (ii) one or more compounds providing amino acids such as Biotrypcase, peptone and/or casamino-acids and yeast extract, (iii) methylated compounds such as methylamines or methanol, and (iv) a sterile extract of a bacterial culture of a bacterium of genus *Eggerthella* according to the invention;

b) placing the inoculum obtained at step a) under anaerobic conditions in a gaseous atmosphere containing dihydrogen $H_2$; and c) incubating under mesothermal conditions to reach an exponential growth phase with release of methane in at least 2 days, preferably no more than 15 days.

The terms «inoculation», «biological sample», «sterile extract», «pure», «anaerobic conditions», «gaseous atmosphere» and «mesothermal conditions» have the same definitions as those mentioned in the preceding sections.

By «microbial consortium» it is meant a group of microorganisms formed of different species (i.e. not in pure culture) and which live in community.

Incubation lasts at least 2 days and preferably no more than 15 days. For example, it is therefore 2, 3, 4, 5, 6, 7, 8, 9, 10, 11, 12, 13, 14 or 15 days.

Incubation is conducted using any technique known to skilled persons e.g. in Hungate tubes.

As aforementioned, the base medium is composed of $KH_2PO_4$, NaCl, $MgSO_4.7H_2O$, $NH_4Cl$, $CaCl_2.2H_2O$, sodium acetate, Cysteine-HCl, resazurin, a Widdel trace element solution, a selenite-tungstate solution, 2% $Na_2S$ and/or 10% $NaHCO_3$ to which are added (ii) one or more compounds providing amino acids such as Biotrypcase, peptone and/or casamino-acids, yeast extract, (iii) methylated compounds such as methylamines or methanol, and (iv) a sterile extract of a bacterial culture of the bacterium of genus *Eggerthella* according to the invention.

In addition, the medium may comprise coenzyme M. This co-factor is essential for methanogenesis. For the archaeon Methanomethylophilus alvus Mx-05, coenzyme M can be omitted.

In particular, in the method of the present invention, the sterile extract of a bacterial culture of a bacterium of genus *Eggerthella* is a bacterial filtrate of a bacterium of genus *Eggerthella*.

More particularly, said filtrate is prepared following the method comprising:

a) cultivating a bacterium of genus *Eggerthella* in a medium e.g. conventional media such as ATCC 260 or 1490 and DSMZ 78 or 209, said medium comprising Biotrypcase, yeast extract, peptone, amino acids, meat extract, hemin, and/or vitamin K1 ru K3, and simple sugars;

b) incubating the culture medium comprising said bacterium at a temperature of 20 to 40° C., preferably at 37° C., for at least 1 day, preferably no more than 15 days;

c) filtering the culture medium comprising said bacterium, preferably using filters preventing the passing of living organisms, in particular on a filter having a pore size of 0.2 µm; and d) collecting the filtrate obtained after step c).

This method is defined in the preceding section on the use of a culture and/or isolation medium comprising a sterile extract of a bacterial culture of a bacterium of genus *Eggerthella*, In particular, in the method of the present invention, the archaeon of the order of commensal clade Methanomassiliicoccales is an archaeon of Archaea Methanomethylophilus alvus, in particular pure, isolated Methanomethylophilus alvus Mx-05 archaeon, a strain deposited on 18 Sep. 2017 under the Budapest Treaty with the Leibniz-Institut (DSMZ, Braunschweig, Germany) under number DSM DSM32684 (Depositor: Université Clermont Auvergne, France).

The present invention also concerns a detection kit of an Archaea archaeon according to the invention, to implement an isolation process of the invention or a culture method of the invention, characterized in that it comprises:

one or more culture media such as aforementioned in the invention, preferably freeze-dried or in solid form; and/or reagents to perform DNA enzymatic amplification of PCR type; and/or a sterile extract of a bacterial culture such as mentioned above in the invention.

The present invention is illustrated in more detail in the following examples.

EXAMPLES

Composition of a Base Medium (BM) Per 1 Litre:

TABLE 3

| Name | Quantity |
|---|---|
| $KH_2PO_4$ | 0.5 g |
| $MgSO_4 \cdot 7H_2O$ | 0.4 g |
| NaCl | 5 g |
| $NH_4Cl$ | 1 g |
| $CaCl_2 \cdot 2H_2O$ | 0.05 g |
| Na-acetate | 1.6 g |
| Cysteine-HCl | 0.5 g |
| Resazurin | 1 mL from a stock solution (1 g/L) |
| Widdel trace element solution | 1 mL from a stock solution (1 g/L) |
| Selenite-tungstate solution | 1 mL |

After autoclaving, the addition is made of:

| | |
|---|---|
| 2% $Na_2S$ (w/v) | 0.1 mL per 5 mL of culture medium |
| 10% $NaHCO_3$ (w/v) | 0.1 mL per 5 mL of culture medium |
| Balch vitamin solution | 0.1 mL per 5 mL of culture medium |

Composition of the Balch Vitamin Solution (Balch et al, 1979)

TABLE 4

| (in mg per litre of distilled water) | |
|---|---|
| Biotin | 2 |
| Folic acid | 2 |
| Pyridoxine hydrochloride | 10 |
| Thiamine hydrochloride | 5 |
| Riboflavin | 5 |
| Nicotinic acid | 5 |
| Calcium pantothenate | 5 |
| Vitamin B12 | 0.1 |
| p-aminobenzoic acid | 5 |
| Lipoic acid | 5 |

Composition and Preparation of a Widdel Trace Element Solution

Ferrous chloride was dissolved in hydrochloric acid. Double distilled water was added and the salts of the different trace elements. The pH was adjusted to between 7.1 and 7.3 with HCl or $Na_2CO_3$.

This trace element solution was used in a proportion of 1 mL per litre of culture medium.

TABLE 5

| | |
|---|---|
| Nitrilotriacetic acid | 1.50 g |
| $MgCl_2$, $6H_2O$ | 2.50 g |
| NaCl | 1.00 g |
| $MnCl_2$, $4H_2O$ | 0.60 g |
| $FeCl_2$, $4H_2O$ | 100.00 mg |
| $CoCl_2$, $6H_2O$ | 100.00 mg |
| $CaCl_2$, $2H_2O$ | 100.00 mg |
| $ZnCl_2$ | 100.00 mg |
| $CuCl_2$, $2H_2O$ | 10.00 mg |
| $AlCl_3$ | 10.00 mg |
| $H_3BO_3$ | 10.00 mg |
| $Na_2MoO_4$, $2H_2O$ | 10.00 mg |
| pH (adjusted with 10 M KOH solution) | 6.50 |
| $H_2O$ double distilled q.s. | 1000 mL |

Enriching with the Archeon Methanomethylophilus Alvus Mx-05

The base medium was prepared under anaerobic conditions in a gaseous $N_2/CO_2$ atmosphere (80:20% v/v). Enrichments were performed on this base medium BM to which were added 1 g/L of yeast extract and 10 to 80 mM of methylated compounds (methanol, methylamines) as final electron acceptors. They were conducted in the presence of an anaerobic gaseous atmosphere formed of dihydrogen $H_2$ as electron donor (2 bar), under mesothermal conditions (incubation at 20 to 40° C.).

The culture medium subsequently used (containing the Balch vitamin solution) was the same medium with the exception that it was depleted of yeast extract (down to complete absence thereof (0 g/L yeast extract) as appropriate) so as to obtain a dominant population of the archaeon Methanomethylophilus alvus Mx-05.

Verification of the abundance of the archaeon Methanomethylophilus alvus Mx-05 was performed by:

Microscopy to determine cell forms and degree of purity of our enrichment;

Measurement of methane production and $H_2$ consumption via gas phase chromatography;

qPCR to quantify the populations of bacteria and archaea, using described primers and protocols known to persons skilled in the art (Borrel et al, 2017);

Sequencing to determine the dominant species of the enrichment.

Dilution experiments in a liquid medium (Hungate tubes containing 5 mL of culture medium) or in solid medium (roll-tubes also containing 5 mL of culture medium) in the presence of $H_2$ and methylated compounds were then carried out. They were conducted after prior filtration (0.45 µm filter) to remove most bacilli, the pure isolated archaeon Methanomethylophilus alvus Mx-05 being in the form of small-sized cocci with cells smaller than 500 µm in diameter. Growth of the archaeon Methanomethylophilus alvus Mx-05 was only obtained in the presence of a sterile extract of a culture of *Eggerthella* sp. prepared by filtration (0.22 µm filter) (see preparation of the filtrate below).

Preparation of the Filtrate of *Eggoerthella* sp.

*Eggerthella* sp. strain Eg01-Mx-05 (strain deposited on 13 Jul. 2017 under the Budapest Treaty with the Leibniz-Institut (DSMZ, Braunschweig, Germany) under number DSM 32565 was cultivated in the base medium containing 10 g/L Biotrypcase, 10 g/L yeast extract, 10 g/L peptone, 10 g/L casamino acids and 20 mM glucose. Incubation was conducted at 37° C. for one week. After filtering (0.22 µm filter) the culture medium of *Eggerthella*, 0.5 mL of filtrate was added per 5 mL of culture medium contained in the tubes used for dilution of the enrichment with the archaeon Methanomethylophilus alvus Mx-05.

Isolation of the Archaeon Methanomethylophilus Alvus Mx-05 in Pure Form

To obtain the pure, isolated archaeon Methanomethylophilus alvus Mx-05 in axenic culture, the serial dilutions in liquid or solid media were conducted using a base medium BM free of complex organic compounds (e.g. yeast extract, Biotrypcase, etc.) but in the presence of the Balch vitamin solution and Widdel Trace element solution, or on the contrary by adding these compounds (yeast extract, Biotrypcase, peptone, casamino acids in a proportion of 2 g/L). This last operation allowed easier detection of the presence of any heterotrophic contaminants in the last positive dilutions. After obtaining colonies in solid medium, these were subcultured in a liquid medium then re-diluted in a liquid medium, the last positive liquid dilution representing the collection strain to be studied.

The pure, isolated strain of the archaeon Methanomethylophilus alvus Mx-05 was deposited with the Leibniz-Institut (DSMZ, Braunschweig, Germany) under number DSM32684 (Depositor: Université Clermont Auvergne, France) on 18 Sep. 2017.

The invention claimed is:

1. An isolation process for isolating an archaeon of the order of commensal clade Methanomassiliicoccales, said isolation process comprising:
    a) inoculating a biological sample comprising an archaeon of the order of commensal clade Methanomassiliicoccales under anaerobic conditions, in a gaseous atmosphere containing dihydrogen ($H_2$) under mesothermal conditions, into a culture medium comprising (i) a base medium comprising $KH_2PO_4$, NaCl, $MgSO_4.7H_2O$, $NH_4Cl$, $CaCl_2.2H_2O$, sodium acetate, Cysteine-HCl, resazurin, a Widdel trace element solution and a selenite-tungstate solution, (ii) 2% $Na_2S$, 10% $NaHCO_3$, and a vitamin mixture, to which is added (iii) one or more compounds providing amino acids, and -(iv) methylated compounds;
    b) replacing the culture medium of a) by an identical culture medium but depleted of compounds providing amino acids and to which vitamins have been added;
    c) detecting enrichment with an archaeon of the order of commensal clade Methanomassiliicoccales in said inoculated sample via microscopy, methane production and $H_2$ consumption, PCR, qPCR, or sequencing; and
    d) performing serial liquid dilutions or the roll-tube technique of said enrichment obtained in c) using a medium as defined in a) or b) to which a sterile extract is added of a bacterial culture a bacterium of genus-*Eggerthella*, until a clone is obtained of an archaeon of the order of commensal clade Methanomassiliicoccales.

2. The isolation process according to claim 1, further comprising c') between c) and d), wherein the culture medium comprising the biological sample is filtered on a filter, the filtrate obtained after c') being subsequently used at d) to perform the serial dilutions.

3. The isolation process according to claim 2, wherein the filter has a pore size of at least 0.45 µm.

4. The isolation process according to claim 1, wherein determination of the obtaining of a clone of an archaeon of the order of commensal clade Methanomassiliicoccales is performed via microscopy, methane production and $H_2$ consumption, PCR, qPCR, or sequencing.

5. The isolation process according to claim 1, wherein the sterile extract of a bacterial culture of a bacterium of genus *Eggerthella* is a bacterial filtrate of a bacterium of genus *Eggerthella*.

6. The isolation process according to claim 5, wherein the bacterial filtrate of a bacterium of genus *Eggerthella* is prepared following the method comprising
    a) cultivating a bacterium of genus *Eggerthella* in a medium, said medium comprising Biotrypcase, yeast extract, peptone, amino acids, meat extract, hemin, a vitamin selected from the group consisting of vitamin K1 and vitamin K3, and monosaccharides having 5 or 6 carbon atoms;
    b) incubating the culture medium comprising said bacterium at a temperature of 20 to 40° C. for at least 1 day;
    c) filtering the culture medium comprising said bacterium; and
    d) collecting the filtrate obtained after c).

7. The isolation process according to claim 1, wherein the archaeon of the order of commensal clade Methanomassiliicoccales is a Methanomethylophilus alvus archaeon.

8. The isolation process according to claim 7, wherein the archaeon Methanomethylophilus alvus is Methanomethylophilus alvus Mx-05, a strain deposited on Sep. 18, 2017 under the Budapest Treaty with the Leibniz-Institut (DSMZ, Braunschweig, Germany) under number DSM32684.

9. The isolation process according to claim 1, wherein the one or more compounds providing amino acids are selected from the group consisting of Biotrypcase, peptone, casamino acids, and yeast extract.

10. The isolation process according to claim 1, wherein the culture media of a) and b) also comprise coenzyme M.

11. The isolation process according to claim 1, wherein the bacterium of genus *Eggerthella* is selected from among *Eggerthella lenta* or the strain *Eggerthella* sp. Eg01-Mx05 deposited on Jul. 13, 2017 under the Budapest Treaty with the Leibniz-Institut (DSMZ, Braunschweig, Germany) under number DSM 32565.

12. A method of culturing an archaeon of the order of commensal clade Methanomassiliicoccales, pure or contained in a microbial consortium, said method comprising:
  a) inoculating into a culture medium either a biological sample comprising an archaeon of the order of commensal clade Methanomassiliicoccales or a pure archaeon of order Methanomassiliicoccales, wherein the culture medium comprises (i) a base medium comprising $KH_2PO_4$, NaCl, $MgSO_4.7H_2O$, $NH_4Cl$, $CaCl_2.2H_2O$, sodium acetate, Cysteine-HCl, resazurin, a Widdel trace element solution, a selenite-tungstate solution, and a compound selected from the group consisting of 2% $Na_2S$ and 10% $NaHCO_3$, to which are added (ii) one or more compounds providing amino acids, (iii) methylated compounds and (iv) a sterile extract of a bacterial culture of a bacterium of genus *Eggerthella*;
  b) placing the inoculum obtained at a) under anaerobic conditions in a gaseous atmosphere comprising dihydrogen $H_2$; and
  c) incubating under mesothermal conditions to reach an exponential growth phase with release of methane in at least 2 days.

13. The method according to claim 12, wherein the culture medium further comprises coenzyme M.

14. The method according to claim 12, wherein the sterile extract of a bacterial culture of a bacterium of genus *Eggerthella* is a bacterial filtrate of a bacterium of genus *Eggerthella*.

15. The method according claim 12, wherein the archaeon of the order of commensal clade Methanomassiliicoccales is a Methanomethylophilus alvus archaeon.

16. The method according to claim 15, wherein the archaeon Methanomethylophilus alvus is Methanomethylophilus alvus Mx-05, a strain deposited on Sep. 18, 2017 under the Budapest Treaty with the Leibniz-Institut (DSMZ, Braunschweig, Germany) under number DSM32684.

17. The method of claim 12, wherein the one or more compounds providing amino acids are selected from the group consisting of Biotrypcase, peptone, casamino acids, and yeast extract.

18. The method according to claim 12, wherein the bacterium of genus *Eggerthella* is selected from among *Eggerthella lenta* or the strain *Eggerthella* sp. Eg01-Mx05 deposited on Jul. 13, 2017 under the Budapest Treaty with the Leibniz-Institut (DSMZ, Braunschweig, Germany) under number DSM 32565.

* * * * *